United States Patent
Li et al.

(10) Patent No.: US 10,463,817 B2
(45) Date of Patent: Nov. 5, 2019

(54) INTELLIGENT BIONIC EXPECTORATION SYSTEM

(71) Applicant: Yaguo Inc., Beijing (CN)

(72) Inventors: Xiaoxue Li, Beijing (CN); Xiaomiao Li, Beijing (CN)

(73) Assignee: YAGUO INC., Beijing (CN)

( * ) Notice: Subject to any disclaimer, the term of this patent is extended or adjusted under 35 U.S.C. 154(b) by 538 days.

(21) Appl. No.: 15/128,877

(22) PCT Filed: Mar. 26, 2015

(86) PCT No.: PCT/CN2015/075100
§ 371 (c)(1),
(2) Date: Sep. 23, 2016

(87) PCT Pub. No.: WO2015/144064
PCT Pub. Date: Oct. 1, 2015

(65) Prior Publication Data
US 2017/0173283 A1 Jun. 22, 2017

(30) Foreign Application Priority Data

Mar. 26, 2014 (CN) .......................... 2014 1 0116218

(51) Int. Cl.
*A61M 16/00* (2006.01)
*A61N 1/36* (2006.01)
(Continued)

(52) U.S. Cl.
CPC .... *A61M 16/0009* (2014.02); *A61M 16/0051* (2013.01); *A61M 16/024* (2017.08);
(Continued)

(58) Field of Classification Search
CPC .......... A61M 16/0009; A61M 16/0816; A61M 16/0833; A61M 16/20; A61M 16/201;
(Continued)

(56) References Cited

U.S. PATENT DOCUMENTS

| 1,044,031 A | * | 11/1912 | Draäger | ................ A61M 16/00 |
| | | | | 128/205.13 |
| 2,770,232 A | * | 11/1956 | Falk | ...................... A61M 16/00 |
| | | | | 128/205.18 |

(Continued)

FOREIGN PATENT DOCUMENTS

| CN | 102309813 A | 1/2012 |
| CN | 102949770 A | 3/2013 |

(Continued)

OTHER PUBLICATIONS

European Communication dated Dec. 4, 2017 for European Application No. 15768007.5.

(Continued)

*Primary Examiner* — Kathryn E Ditmer
(74) *Attorney, Agent, or Firm* — David D. Brush; Westman, Champlin & Koehler, P.A.

(57) ABSTRACT

An intelligent bionic expectoration system and a three-way device thereof. The intelligent bionic expectoration system includes a negative pressure suction module, a central processing module, a patient interface unit and a respiratory muscle synchronous motion module. The central processing module controls two valves to open or close, closing one valve while opening another valve, and controls the respiratory muscle synchronous motion module. The patient interface unit is connected to the positive pressure ventilation module and the negative pressure suction module, allowing positive or negative pressure airflow to flow by, depending on which valve is open, so as to allow airflow to flow in or out of the lung. The respiratory muscle synchronous motion module can employ nerve stimulation and mechanical pushing, and acts synchronously as the airflow moves, thereby simulating human coughing and achieves bionic expectoration.

22 Claims, 5 Drawing Sheets

(51) Int. Cl.
*A61M 16/08* (2006.01)
*A61M 16/20* (2006.01)
*A61N 2/00* (2006.01)

(52) U.S. Cl.
CPC .... *A61M 16/0816* (2013.01); *A61M 16/0833* (2014.02); *A61M 16/201* (2014.02); *A61M 16/202* (2014.02); *A61M 16/206* (2014.02); *A61N 1/3601* (2013.01); *A61N 2/006* (2013.01); *A61M 2016/003* (2013.01); *A61M 2016/0015* (2013.01); *A61M 2205/054* (2013.01); *A61M 2205/057* (2013.01); *A61M 2205/18* (2013.01); *A61M 2205/3331* (2013.01); *A61M 2205/50* (2013.01); *A61M 2205/502* (2013.01)

(58) Field of Classification Search
CPC .. A61M 16/202; A61M 16/206; A61M 39/10; A61N 1/3601; A61N 2/006
See application file for complete search history.

(56) References Cited

U.S. PATENT DOCUMENTS

| | | | | |
|---|---|---|---|---|
| 2,915,056 | A * | 12/1959 | Lee | A61M 16/104 128/203.14 |
| 2,972,345 | A * | 2/1961 | Spigel | A61M 16/00 128/204.23 |
| 3,026,908 | A * | 3/1962 | Blair | F16K 11/16 137/596.2 |
| 3,515,163 | A * | 6/1970 | Freeman | A61M 16/208 137/102 |
| 3,662,751 | A * | 5/1972 | Barkalow | A61M 16/00 128/204.25 |
| 3,875,810 | A * | 4/1975 | Paramonoff | F15B 21/00 74/55 |
| 3,942,547 | A * | 3/1976 | Pfitzner | A61B 5/097 137/102 |
| 4,522,221 | A * | 6/1985 | Chivens | E04H 4/16 137/118.07 |
| 4,637,386 | A * | 1/1987 | Baum | A61M 16/00 128/204.21 |
| 4,712,580 | A * | 12/1987 | Gilman | A61M 16/20 128/204.18 |
| 5,063,925 | A * | 11/1991 | Frank | A61M 16/20 128/204.18 |
| 5,072,729 | A * | 12/1991 | DeVries | A61M 16/20 128/204.21 |
| 6,073,630 | A * | 6/2000 | Adahan | A61M 16/20 128/204.23 |
| 6,427,691 | B1 * | 8/2002 | Jinotti | A61M 16/20 128/205.19 |
| 7,077,131 | B2 * | 7/2006 | Hansen | A61M 16/026 128/204.18 |
| 2003/0051729 | A1 * | 3/2003 | Be'eri | A61M 16/20 128/204.18 |
| 2004/0107960 | A1 | 6/2004 | Wu et al. | |
| 2007/0186928 | A1 * | 8/2007 | Be'Eri | A61M 16/00 128/204.18 |
| 2007/0199566 | A1 * | 8/2007 | Be'eri | A61M 16/0051 128/204.23 |
| 2012/0029321 | A1 * | 2/2012 | Makaretz | A61M 16/04 600/301 |
| 2012/0285460 | A1 | 11/2012 | Smith et al. | |
| 2013/0255689 | A1 * | 10/2013 | Kim | A61M 16/208 128/205.24 |
| 2014/0116441 | A1 | 5/2014 | McDaniel | |
| 2015/0059750 | A1 * | 3/2015 | Arnott | A61M 16/202 128/204.21 |
| 2015/0231348 | A1 * | 8/2015 | Lee | A61N 1/3601 128/204.22 |
| 2015/0283340 | A1 | 10/2015 | Zhang et al. | |
| 2016/0317780 | A1 * | 11/2016 | Cole | A61M 16/0816 |

FOREIGN PATENT DOCUMENTS

| | | |
|---|---|---|
| CN | 103619392 A | 3/2014 |
| CN | 103933648 A | 7/2014 |
| CN | 203935485 U | 11/2014 |
| JP | H1030973 A | 2/1998 |
| JP | 2003079732 A | 3/2003 |
| JP | 2009509610 A | 3/2009 |
| JP | 2010220717 A | 10/2010 |
| WO | 2007054829 A2 | 5/2007 |
| WO | 2012042255 A1 | 4/2012 |
| WO | 2013001398 A1 | 1/2013 |
| WO | 2014030099 A1 | 2/2014 |

OTHER PUBLICATIONS

Korean Office action from KIPO dated Jan. 10, 2018 for KR application 2016-7029904.
English Translation of Korean Office action from KIPO dated Jan. 10, 2018 for KR application 2016-7029904.
English translation of the International Written Opinion dated Aug. 9, 2016, for corresponding International Application No. PCT/CN2015075100, filed Mar. 26, 2015.
Office Action dated Sep. 28, 2018 from the Japanese Patent Office for Japanese Application No. 2017501452.
English translation of the Office Action dated Mar. 15, 2016 for corresponding Chinese Application No. 201410116218.3.
International Search Report dated May 13, 2015, for corresponding International Application No. PCT/CN2015075100, filed Mar. 26, 2015.

* cited by examiner

INTELLIGENT BIONIC EXPECTORATION SYSTEM

CROSS-REFERENCE TO RELATED APPLICATION

This Application is a Section 371 National Stage Application of International Application No. PCT/CN2015/075100, filed Mar. 26, 2015, and published as WO 2015/144064 A1 on Oct. 1, 2015, not in English, which claims priority to and benefits from Chinese Patent Application No. 201410116218.3, filed Mar. 26, 2014, with the State Intellectual Property Office of P. R. China on Mar. 26, 2014, the contents of which are hereby incorporated by reference in their entireties.

FIELD

The present disclosure relates to the field of medical health, in particularly to an intelligent bionic system for expectorating sputum.

BACKGROUND

Cough reflex is a common important defense mechanism, and effectors thereof are located at larynx, trachea and bronchial mucosa. The effector located above primary bronchus is sensitive to mechanical stimulation, and the effector located below secondary bronchus is sensitive to chemical stimulation. The cough reflex is triggered when afferent impulse is introduced into medulla oblongata.

To cough, a short or deep inhaling (normally 2.5 L) happens firstly; then glottis is closed; expiratory muscle (abdominal muscle and internal intercostal muscle) are contracted intensively; intrapulmonary pressure and intrapleural pressure are increased sharply (may be up to 100 mmHg or even more); then the glottis is opened suddenly; gas inside lung is discharged at high speed as the intrapulmonary pressure is very high, such that foreign matters or secretions inside respiratory tract are discharged.

A patient suffering from myasthenia of abdominal muscle and respiratory muscle has a weakened cough reflex. Due to limited thoracic expansion in a patient lying in bed, gas getting into lung before cough is insufficient, thereby resulting in weakened or even invalid cough. Besides, the cough reflex is also limited in a patient with suppressed medullary center.

Patients with weakened respiratory muscle caused by various clinical reasons often need a ventilator for assisting to breathe. Cough in this kind of patients is weak such that it is impossible to expectorate secretions deep down inside lung effectively, resulting in very high morbidity of ventilator-associated pneumonia. It is very important to assist a patient to expectorate secretions deep down inside lung, so as to prevent the ventilator-associated pneumonia. Currently, a commonly-used method for sputum suction is carried out with a closed sputum suction tube.

The term "closed phlegm suction" refers to a sputum suction operation without disconnecting from the ventilator or stopping mechanical ventilation. Moreover, the sputum suction tube is covered with a transparent membrane, and entire sputum suction operation is completed under closed environment. As there are up to 20 or more levels of bronchus inside lung, the sputum suction tube is merely capable of sucking sputum in the primary bronchial. In addition, as the lung is of an asymmetrical structure, the sputum suction tube is merely capable of sucking sputum in right lung, other than sputum in left lung. For this reason, the ventilator-associated pneumonia usually occurs in the left lung. Furthermore, the sputum suction tube increases risks in causing airway scratch, introducing bacteria and influencing hemodynamics.

Except for such a device for sputum suction (eg. the closed sputum suction tube) manually operated, an automatic device for expectorating sputum is presented by now. A principle of Cough Assist machine for expectorating sputum provided by Royal Philips is to provide the airway high positive pressure ventilation, which is rapidly converted into negative pressure suction, such that sputum deep down inside lung is discharged by simulating airflow during cough.

However, it is impossible to use the Cough Assist machine as a regular means for expectorating sputum due to requirement to disconnect from the ventilator when using, which is inconvenient and has a high risk for a patient suffering from severe illness. Besides, the Cough Assist machine finishes inhaling by taking time as a control variable of periodic cycle; however, it is safer and more effective to take volume or flow as the control variable of periodic cycle. In addition, it is impossible for the Cough Assist machine to maintain the patient's exhaling to be a positive end expiratory pressure (PEEP), thereby being inappropriate for a patient who needs high PEEP, because such these patients are in danger of alveolar collapse if without the high PEEP. As to another obvious defect, the Cough Assist machine is not provided with an alarming system, which is necessary to a life support system. Finally, as the Cough Assist machine is provided with a pipeline only shared by exhaling and inhaling, it is possible to inhale secretions expectorated previously during next inhaling, which may increase a risk of secondary infection due to the patient himself/herself, shorten a product life of the pipeline, and increase a risk of infecting other patients who use this Cough Assist machine next time.

In addition, WO 2007/054829 A2 provides a mechanical in-exsufflation device, which by ventilator inhales airflow and subsequently exhale airflow in a rapid and short manner for simulating human cough, such that sputum accumulated in airway and trachea branches can be discharged easily. Such a system controls inhaling and exhaling automatically by detecting the airflow, so as to relieve burden of working force. The sputum is expectorated by several times of intermittent negative pressure exhaling, which not only prevents pulmonary alveoli from collapsing caused by over high negative pressure, but also affects a dozen levels of bronchus, thereby discharging sputum deep down inside lung. However, all movements of human cough includes deeply inhaling, closing glottis, lowering the diaphragm muscle, rapidly contracting the expiratory muscle and abdominal muscle, increasing intrapulmonary pressure, opening glottis, contracting the diaphragm muscle, discharging the airflow with high pressure from lung. Such a device for expectorating sputum simulates airflow during cough; whereas cough-related respiratory muscle is not involved in the movements. For a patient ventilated mechanically, long-term anoxia and systemic nutrition deficiency causes reduction and atrophy of diaphragm muscle fibre, such that activity of the diaphragm muscle is decreased. Firstly, merely simulating movements of airflow during cough, such a device does not intervene PEEP process such that it is impossible to guarantee sufficient tidal volume before cough if without special control, thereby being unable to form effective cough. Secondly, the PEEP process by a ventilator causes mechanical lung injury itself, and such a device for expectorating sputum merely simulates movements of airflow during cough without accompanying movements in accordance with muscle, inappropriate control may cause additional mechanical lung injury. Thirdly, it is bad for discharging sputum by adversely influencing intensity of cough and expectoration movement due to merely depending on the airflow with negative pressure without assisting with contraction of abdominal muscle. Finally, the patient assisted with discharging sputum may be disconnected from ventilator earlier than expecting; however, it may adversely influence a patient suffering from atrophy of diaphragm muscle by earlier disconnecting from the ventilator.

SUMMARY (I) Technical Problem to be Solved

Aiming at solving defects existing in the prior art, the present disclosure provides in embodiments an intelligent bionic system for expectorating sputum, by which human cough is simulated in terms of both airflow movement and respiratory muscle movement intelligently, so as to assist a patent to discharge secretions deep down inside his/her lung safely and effectively, lower morbidity of ventilator-associated pneumonia, and recover diaphragm muscle, thus disconnecting from ventilator earlier than expected.

(II) Technical Solution

In one aspect, the present disclosure provides in embodiments an intelligent bionic system for expectorating sputum, including:

a negative pressure suction module, configured to generate first airflow with a negative pressure for discharging gas from patient's lung;

a patient connecting unit, configured to allow the first airflow with the negative pressure and second airflow with a positive pressure to flow through, and configured to connect the negative pressure suction module, a patient and a positive pressure ventilation module which may be a ventilator;

a central processing module, connected to the patient connecting unit; and a respiratory muscle synchronizing module, connected to the central processing module and configured to enable a respiratory muscle to generate a certain movement in coordination with the first airflow and the second airflow, by means of nerve stimulation or mechanical stimulation.

Further, the patient connecting unit includes a three-way device, a sputum collecting connector and a sputum collecting cup, the three-way device comprises a first valve configured to selectively block airflow from the positive pressure ventilation module to the patient connecting module, and a second valve is disposed between the three-way device and the negative pressure suction module and configured to selectively block airflow from the patient connecting module to the negative pressure suction module.

Further, when the positive pressure ventilation module is working, the central processing module is configured to open the first valve and close the second valve, and controls the respiratory muscle synchronizing module to generate a muscle movement of inhaling, i.e., contraction of diaphragm muscle.

Further, when the negative pressure suction module is working, the central processing module is configured to open the second valve and close the first valve, and control the respiratory muscle synchronizing module to generate a muscle movement of cough, i.e., contraction of abdominal muscle.

Further, the intelligent bionic system for expectorating sputum further includes a sensor module and a display module both connected to the central processing module.

Further, a first pressure detecting point of the sensor module is located at a side wall of a first branch of the three-way device directly connected to the positive pressure ventilation module, a second pressure detecting point and a third pressure detecting point of the sensor module are located at a side wall of a second branch of the three-way device directly connected to the patient, a distance between the second pressure detecting point and the patient is greater than that between the third pressure detecting point and the patient.

Further, the central processing module is configured to determine whether the first valve is closed based on pressure values detected at the first pressure detecting point and the third pressure detecting point.

Further, the central processing module determines that the first valve is closed when a pressure difference detected between the first pressure detecting point and the third pressure detecting point is beyond a threshold value. As safety prevention, an alarm is given if the first valve is not opened when inhaling.

Further, the central processing module is configured to calculate a flow rate and a direction of airflow breathed by the patient based on a pressure difference detected between the second pressure detecting point and the third pressure detecting point.

Further, the central processing module is configured to determine whether the patient finishes inhaling and exhaling based on the flow rate and the direction detected at three pressure detecting points, so as to switch between inhaling and exhaling in time.

Further, the positive pressure ventilation module is a ventilator and its pipeline.

Further, the negative pressure suction module is a negative pressure source such as a turbofan and its pipeline.

Further, the first valve is a pneumatic diaphragm valve.

Further, the second valve is an electric-controlled switching valve.

Further, the first airflow with the negative pressure is of a flow rate allowed by the negative pressure suction module of 14 L/minute to 800 L/minute.

Further, the nerve stimulation is by way of electrical stimulation or magnetic stimulation.

Further, the electrical stimulation is executed by a pair of treating electrodes acting on both sides of phrenic nerves and a pair of reference electrodes acting on a surface of pectoralis major muscle.

Further, the magnetic stimulation is executed by discharging from a capacitor stored with electric energy to stimulate coils such that a pulse current is generated.

Further, the mechanical stimulation is executed by different pushes acting on the respiratory muscle with a mechanical arm, in corporation with inhaling and exhaling, wherein the different pushes are generated in the light of a control signal from the central processing module.

Figure 2:
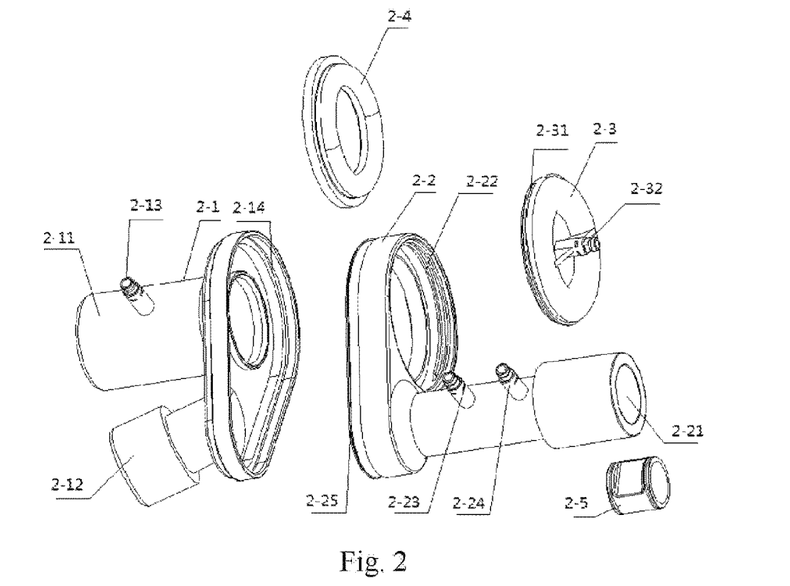
FIG. 2 is a schematic view showing a three-way device provided with pressure detecting points according to an embodiment of the present disclosure.

In another aspect, the present disclosure provides in embodiments a three-way device having a function of opening and closing airway. The three-way device includes a first part 2-1, a second part 2-2, a pressing cover 2-3, a diaphragm valve 2-4, an air-resistor 2-5. The first part 2-1 includes a second end 2-11 for connecting a positive pressure ventilation module, a first end 2-12 for connecting a negative pressure suction module, a first pressure detecting point 2-13 and a groove 2-14. Specifically, the first pressure detecting point 2-13 is located at a side wall of the second end 2-11 for connecting the positive pressure ventilation module. The second end 2-11 for connecting the positive pressure ventilation module and the first end 2-12 for connecting the negative pressure suction module are located at the one side of the first part 2-1, and the groove 2-14 is located at the other side of the first part 2-1. The second part 2-2 includes a third end 2-21 for connecting a patient, an internal thread 2-22, a second pressure detecting point 2-23 and a third pressure detecting point 2-24, and a snap 2-25. Specifically, the second pressure detecting point 2-23 and the third pressure detecting point 2-24 are located at a side wall of the third end 2-21 for connecting the patient. Moreover, a distance between the second pressure detecting point 2-23 and snap 2-25 is shorter than that between the third pressure detecting point 2-24 and the snap 2-25 and a distance between the second pressure detecting point 2-23 and the patient is greater than that between the third pressure detecting point 2-24 and the patient. The pressing cover 2-3 including an external thread 2-31 and an air supply hole 2-32 is located opposing to the second end 2-11 for connecting the positive pressure ventilation module. Moreover, the snap 2-25 of the second part 2-2 is fitted to the groove 2-14, which is not limited herein and other structures may also be used. The second part 2-2 is screwed to the pressing cover 2-3 through the internal thread 2-22 and the external thread 2-31. The diaphragm valve 2-4 is disposed inside second part 2-2 and at a position corresponding to the pressing cover 2-3. The air-resistor 2-5 is disposed in the third end for connecting the patient, so as to change pressure of the airflow flowing through the air-resistor 2-5, thereby facilitating to monitor air flow.

In case medical staffs make a mistake when connecting pipelines, the first pressure detecting point 2-13, the second pressure detecting point 2-23, the third pressure detecting point 2-24 and an air supply hole 2-32 are provided with a structure for preventing misplug. For example, four grooves or projections distributed uniformly are disposed around the first pressure detecting point 2-13, three grooves or projections distributed uniformly are disposed around the second pressure detecting point 2-23, and two grooves or projections distributed symmetrically are disposed around the third pressure detecting point 2-24. Certainly, the above structures for preventing misplug are only illustrative and other structures may also be used.

Similarly, the second part 2-2, the first part 2-1 and the pressing cover 2-3 are also provided with the structure for preventing misplug, thereby avoiding misoperation when connecting pipelines by medical staffs.

Figure 3:
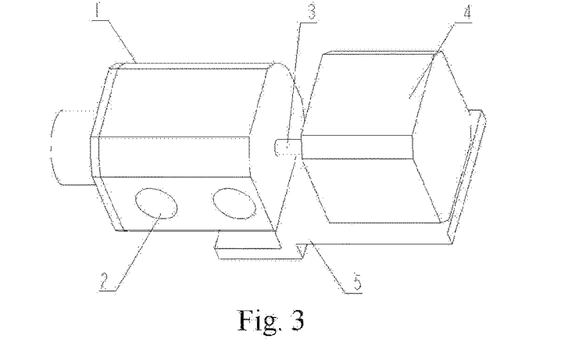
FIG. 3 is a schematic view showing a switching valve configured to open and close pipeline according to an embodiment of the present disclosure.
Figure 4:
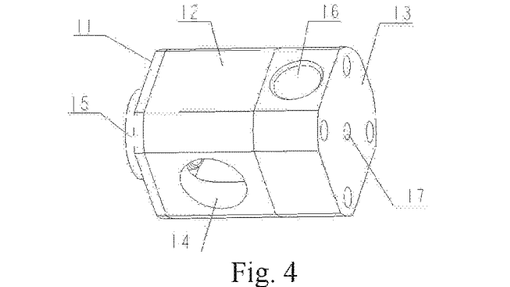
FIG. 4 is a schematic view showing a chamber of a switching valve configured to open and close pipeline according to an embodiment of the present disclosure.
Figure 5:
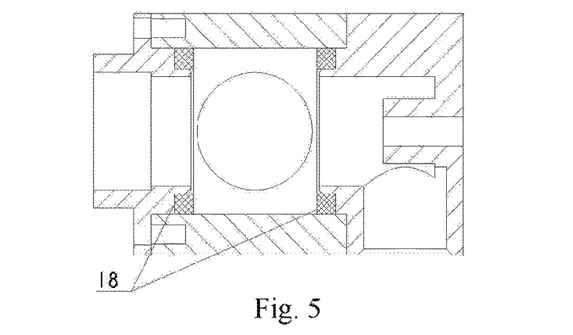
FIG. 5 is a sectional view showing a chamber of a switching valve configured to open and close pipeline according to an embodiment of the present disclosure.

The present disclosure further provides in embodiments an electric-controlled switching valve, including:
a holder 5,
an electric power driving device 4, installed at the holder 5,
a chamber 1, also installed at the holder 5 and including a front cover 11 provided with a suction hole 15; a chamber body 12; and a rear cover 13 provided with a travel hole 17, wherein
the front cover 11, the chamber body 12 and the rear cover 13 are fasten-connected by bolts together;
the chamber 1 is also provided with a driving air hole 14 at one side surface close to the front cover 11 and a free air hole 16 at an upper or side surface close to the rear cover 13; and
the chamber 1 is further provided with a sealing washer 18 at both sides of the driving air hole 14,
an air duct 2, connected to the driving air hole 14,
a direction-changing assembly 3, including a spring 39, a mandril 32 and a direction-changing sliding block 31, wherein
the spring 39, located at a step inside the chamber 1, is pressed against the front cover 11 of the chamber 1 at one end and is in a contact with the direction-changing sliding block 31 at the other end;
the mandril 32 is connected to the direction-changing sliding block 31 through the travel hole 17, and configured to move along an axis of the chamber 1 under a drive of the electric power driving device 4;
the direction-changing sliding block 31, located inside the chamber 1, is in a sealing contact with an inner wall of the chamber 1 at its periphery, and configured to move in a linear reciprocation manner along the axis of the chamber 1 under alternative effects of the spring 39 and the mandril 32,
wherein the switching valve, controlled by the intelligent bionic system for expectorating sputum, is configured to control airflow generated by a blower to flow.

Preferably, the chamber 1 may be in a detachable type.

Figure 6:
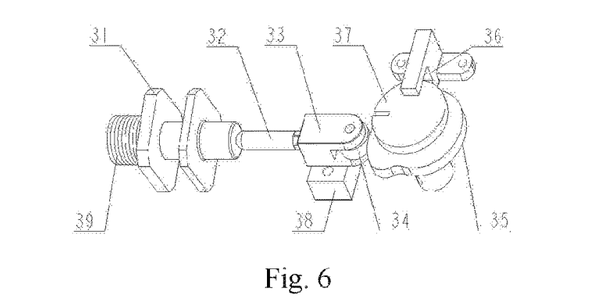
FIG. 6 is a schematic view showing a direction-changing assembly of a switching valve configured to open and close pipeline according to an embodiment of the present disclosure.
Figure 7:
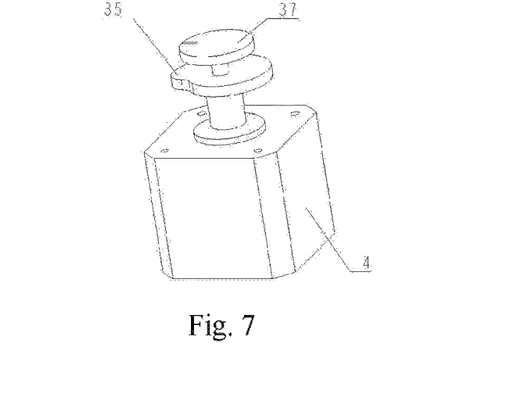
FIG. 7 is a schematic view showing a cam of a switching valve configured to open and close pipeline according to an embodiment of the present disclosure.
Figure 8:
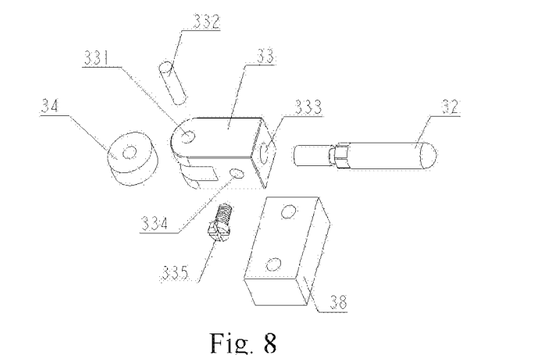
FIG. 8 is a schematic view showing a pushing block of a switching valve configured to open and close pipeline according to an embodiment of the present disclosure.
Figure 9:
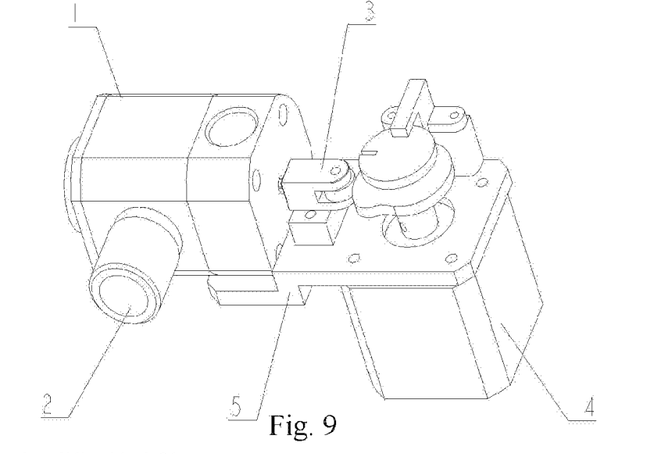
FIG. 9 is a schematic view showing another switching valve configured to open and close pipeline according to an embodiment of the present disclosure.

Alternatively, the direction-changing assembly 3 includes the direction-changing sliding block 31, the mandril 32, a pushing block 33, a roller 34, a cam 35, a displacement sensor 36, a displacement turntable 37, a supporting platform 38 and the spring 39,
the electric power driving device 4 is an electric motor,
the pushing block 33, placed on the supporting platform 38, is provided with
a first via hole 331, located at its upper surface close to a fourth end having an opening, through which the pushing block 33 is connected to the roller 34 rotated freely with a pivot 332;
a second via hole 333, located at its right surface of a fifth end opposing to the fourth end, through which the pushing block 33 is connected to the mandril 32 in a plug-in manner; and
a thread hole 334, located at its side surface close to the fifth end, through which the mandril 32 is fixed thereto by a bolt 335,
the supporting platform 38, fixed on the holder 5, is configured to support the pushing block 33,
the cam 35 is fastened to the electric power driving device 4 at its bottom, so as to rotate under a drive of the electric power driving device 4; and fastened to the displacement turntable 37 at its top so as to rotate therewith, and
the displacement sensor 36, fixed on the holder 5, is configured to detect the displacement turntable 37, for determining a rotating range of the electric power driving device 4.

Further, the direction-changing assembly 3 includes the direction-changing sliding block 31, the mandril 32, a cam 35, a displacement sensor 36, a displacement turntable 37 and the spring 39,
the electric power driving device 4 is an electric motor;
the cam 35 is fasten to the electric power driving device 4 at its bottom so as to rotate under a drive of the electric power driving device 4; and fastened to the displacement turntable 37 at its top so as to rotate therewith,
the mandril 32 is in a direct contact with the cam 35, such that the mandril 32 moves along the axis of the chamber 1 under a drive of the cam 35;

the displacement sensor 36, fixed on the holder 5, is configured to detect the displacement turntable 37, for determining a rotating range of the electric power driving device 4.

Figure 14:
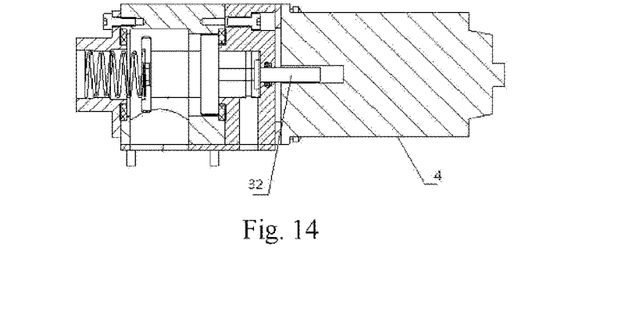
FIG. 14 is a schematic view showing an operation state of a switching valve configured to open and close pipeline according to an embodiment of the present disclosure.

Preferably, the direction-changing assembly 3 includes the direction-changing sliding block 31, the mandril 32 and the spring 39;

the electric power driving device 4 is an electromagnet; and the mandril 32 is configured to move along the axis of the chamber 1 under a push of the electromagnet.

(III) Beneficial Effects

In the present disclosure, the respiratory muscle movement is combined with the mechanical inexsufflation, so as to simulate human cough more intelligent, to assist a patient to expectorate secretions deep down inside lung more safely and effectively, and assist to lower a risk of suffering ventilator-associated pneumonia for a patient ventilated with an invasive ventilator. The central controlling module starts negative pressure exhaling at the time when positive pressure inhaling is about to be finished by the ventilator, which is in accordance with respiratory muscle movement, so that the patient's rapid exhaling cooperating with suitable movement of respiratory muscle at the same time is achieved, which realizes not only more effective deep inhaling and quick exhaling, thereby forming valid cough, achieving better synchronization between patient and ventilator and thus reducing patient-ventilator asynchrony; but also allows diaphragm muscle to be more involved in the mechanical ventilation, thereby relieving negative pressure suction-related injury effectively.

In addition, the respiratory muscle movement is introduced into mechanical inexsufflation for expectorating sputum, so as to assist a patient suffering from severe illness to avoid, to a greatest extent, mechanical ventilator induced lung injury (VILI) and ventilator-associated pneumonia (VAP), and at the same time to improve function of the diaphragm muscle, maintain activity of the diaphragm muscle, prevent ventilator induced diaphragmatic dysfunction (VIDD) caused by the ventilator effectively, thus bringing an unprecedented solution to this three complications, which are always perplexed by ICU doctor, such that the patient may be wean from the ventilator earlier than expected. In addition, it is possible to avoid using drugs for VILI and VAP, thereby reducing medical burden and side effects for patents.

REFERENCE NUMERALS

1: chamber; 2: air duct; 3: direction-changing assembly; 4: electric motor; 5: holder; 11: front cover; 12: chamber body; 13: rear cover; 14: driving air hole; 15: suction hole; 16: free air hole; 17: travel hole; 18: sealing washer; 31: direction-changing sliding block; 32: mandril; 33: pushing block; 34: roller; 35: cam; 36: displacement sensor; 37: displacement turntable; 38: supporting platform; 39: spring; 331: first via hole; 332: pivot; 333: second via hole; 334: thread hole; 335: bolt; 151: three-way device; 152: sputum collecting connector; 153: sputum collecting cup; first part of the three-way device: 2-1; second part of the three-way device: 2-2; pressing cover: 2-3; diaphragm valve: 2-4; air-resistor: 2-5; second end for connecting positive pressure ventilation module: 2-11; first end for connecting negative pressure suction module: 2-12; pressure detecting point: 2-13; groove: 2-14; third end for connecting patient: 2-21; internal thread: 2-22; second pressure detecting point: 2-23; third pressure detecting point: 2-24; snap: 2-25; external thread: 2-31; air supply hole: 2-32.

DETAILED DESCRIPTION

With reference to drawings, an intelligent bionic system for expectorating sputum of the present disclosure is described in details as follows.

Figure 1:
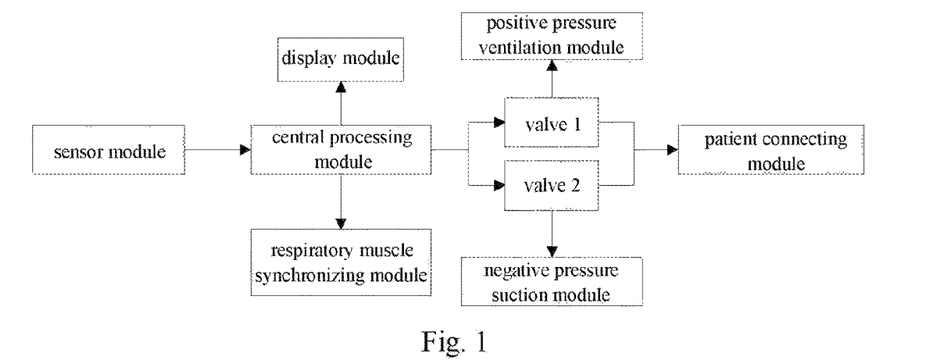
FIG. 1 is a schematic view showing an intelligent bionic system for expectorating sputum according to an embodiment of the present disclosure.

In one aspect, the present disclosure provides in embodiments an intelligent bionic system for expectorating sputum as shown in FIG. 1, including: a positive pressure ventilation module, a negative pressure suction module, a patient connecting module, a central processing module, a display module, a sensor module and a respiratory muscle synchronizing module, in which the positive pressure ventilation module is configured to generate second airflow with a positive pressure, and may be a ventilator; the negative pressure suction module is configured to generate first airflow with a negative pressure; the patient connecting unit allows the second airflow with the positive pressure and the first airflow with the negative pressure to flow through; the positive pressure ventilation module and the negative pressure suction module may be connected to a patient through the patient connecting unit and the patient connecting unit may include a three-way device. The three-way device includes a first valve selectively blocking airflow from the positive pressure ventilation module to the patient connecting module, and a second valve is disposed between the three-way device and the negative pressure suction module and selectively blocks the airflow from the patient connecting unit to the negative pressure suction module. Preferably, the first valve may be a pneumatic diaphragm valve.

The following steps may be realized by the central processing module based on results fed back from the sensor module: selectively opening or closing the first valve to allow or stop the second airflow with the positive pressure of the ventilator for inflating patient's lung; selectively opening or closing the second valve to allow or stop the first airflow with the negative pressure for deflating the patient's lung; and controlling the respiratory muscle synchronizing module to generate muscle movement when inhaling or exhaling.

The respiratory muscle synchronizing module may achieve pacemaking of the diaphragm muscle by means of nerve stimulation or mechanical stimulation, so as to enable the respiratory muscle to move. The nerve stimulation includes electrical stimulation and magnetic stimulation. Specifically, a stimulation signal is generated by a square-wave pulse of a single chip microcomputer and followed by shaped and enlarged. An electrical stimulation device includes two pairs of electrodes, one pair are treating electrodes acting on both sides of phrenic nerves of a patient and the other pair are reference electrodes acting on a surface of pectoralis major muscle of the patient. The magnetic simulation device includes a charging capacitor and a stimulation coil. The capacitor stored with electric energy is discharged to the stimulation coil such that a pulse current is generated to stimulate human body. The mechanical stimulation is executed by two mechanical arms acting on diaphragm muscle and abdominal muscle respectively and corresponding pushing actions by the mechanical arms are generated in the light of a control signal of the central processing module.

A sensitive sensor module ensures the system an effective alarming system. If it is determined that a valve does not move as expected at a certain breathing stage, a highest level of alarming is thus generated, and other problems may cause a lower level of alarming.

Figure 15:
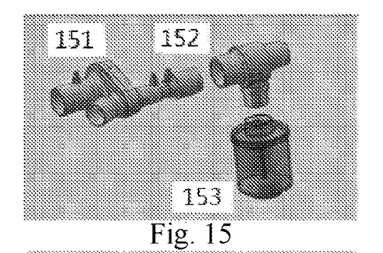
FIG. 15 is a schematic view showing a patient connecting unit connected to none of other components according to an embodiment of the present disclosure.
Figure 16:
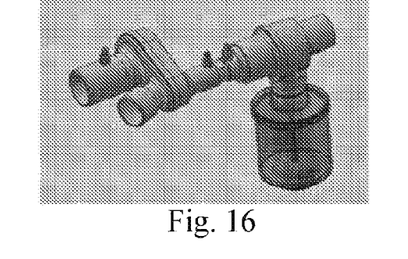
FIG. 16 is a schematic view showing a patient connecting unit connected to other components according to an embodiment of the present disclosure.

As shown in FIGS. 15 and 16, the patient connecting unit includes a three-way device 151, a sputum collecting connector 152 and a sputum collecting cup 153. The three-way device 151 is provided with three pressure detecting points, connected to three pressure sensors in the sensor module respectively. Specifically, two of three pressure detecting points may be configured to calculate flow rate in pressure, so that the three pressure sensors may monitor patient's breathing in a real-time manner.

With reference to FIG. 2, detailed description is made to the structure of the three-way device and the arrangement of the three pressure detecting points.

As shown in FIG. 2, the three-way device includes a first part 2-1, a second part 2-2, a pressing cover 2-3, a diaphragm valve 2-4, an air-resistor 2-5. The first part 2-1 includes a second end 2-11 for connecting a positive pressure ventilation module, a first end 2-12 for connecting a negative pressure suction module, a first pressure detecting point 2-13 and a groove 2-14. The first pressure detecting point 2-13 is located at a side wall of a first branch of the first part 2-1 directly connecting to the second end 2-11 for connecting the positive pressure ventilation module. The second part 2-2 includes a third end 2-21 for connecting a patient, an internal thread 2-22, a second pressure detecting point 2-23, a third pressure detecting point 2-24, and a snap 2-25. The second pressure detecting point 2-23 and the third pressure detecting point 2-24 are located at a side wall of a second branch of the second part 2-2 directly connecting to the patient, and a distance between the second pressure detecting point 2-23 and the patient is different from that between the third pressure detecting point 2-24 and the patient. The second pressure detecting point 2-23, the third pressure detecting point 2-24 and an air supply hole 2-32 are provided with a structure for preventing misplug, thereby avoiding misoperation when connecting pipelines by medical staffs. The snap 2-25 is fitted to the groove 2-14 of the first part 2-1, thus improving air impermeability of the device. The first pressure detecting point 2-13 introduces airflow under detection to a first pressure sensor, so as to monitor air pressure at the second end 2-11 for connecting the positive pressure ventilation module in a real-time manner. The third pressure detecting point 2-24 introduces airflow under detection to a second pressure sensor, so as to monitor air pressure at the third end 2-21 for connecting the patient in a real-time manner. It may be determine whether the diaphragm valve 2-4 is closed via cooperation between the first pressure detecting point 2-13 and the third pressure detecting point 2-24. The diaphragm valve 2-4 is determined to be closed when a pressure difference detected between the first pressure detecting point 2-13 and the third pressure detecting point 2-24 is beyond a threshold value. The second pressure detecting point 2-23 and the third pressure detecting point 2-24 introduce airflow under detection to one differential sensor, which is cooperated with the air-resistor 5 so as to monitor the flow rate and the direction of the air flowing through the third end 2-21 for connecting the patient in a real-time manner. A pressure difference may be obtained from pressures detected from the second pressure detecting point 2-23 and the third pressure detecting point 2-24, and the flow rate and the direction of the air may be calculated considering the shape of the air-resistor 5.

The first valve includes one pneumatic diaphragm, which is placed flatwise in an inner chamber of a first branch of the three-way device when not blown up; and is swelled to block inside the inner chamber of the first branch when blown up. When the first valve is opened, the airflow is transferred from the ventilator to patient's lung at a positive pressure, and at the same time, the second valve is closed to prevent the patient's lung from exposing to the negative pressure. When the second valve is opened, the patient's lung is exposed to the negative pressure (an allowed negative pressure flow rate is 14 L/minute to 800 L/minute), and at the same time, the first valve is closed to prevent the ventilator is exposed to the negative pressure.

The main feature of the system is capable of mechanically assisting a patient in inhaling and exhaling (cough) along with a synchronous movement of the respiratory muscle. The muscle movement during coughing refers to rhythmicity expansion and contraction of thorax caused by contraction and relaxation of the respiratory muscle. The main inhaling muscle includes external intercostal muscle of diaphragm muscle, the main exhaling muscle includes internal intercostal muscle and abdominal muscle, and assisting inhaling muscle includes scalene muscle and sternocleidomastoid, which play function with force inhaling only. The diaphragm muscle is mainly contracted when inhaling; whereas the abdominal muscle and the internal intercostal muscle are mainly contracted when coughing. Upon starting cough, during the inhaling stage, at the time that the first valve is opened and the second valve is closed, the respiratory muscle synchronizing module may generate a contraction action of the diaphragm muscle, such that the patient inhales more sufficient, getting ready for valid cough. When it is determined that the patient finishes inhaling detected by the pressure detecting points, the second valve is opened and the first valve is closed, the respiratory muscle synchronizing module may generate a contraction action of the abdominal muscle, thus simulating cough in terms of airflow and muscle movement, so that a better effect of discharging secretions from lung is achieved. When it is determined that patient finishes exhaling by the pressure detecting points, the second valve is closed and the first valve is opened, so as to start a new breathing cycle.

In a further aspect, the present disclosure provides in embodiments an electronic-controlled switching valve, configured to open and close pipeline. Reference will be made hereinafter in detail to the electronic-controlled switching valve in exemplary embodiments in conjunction with figures.

In a first embodiment, as shown in FIG. 3, the electronic-controlled switching valve with the function of opening and closing pipeline according to the present disclosure includes a chamber 1, an air duct 2, a direction-changing assembly 3, an electric power driving device 4 and a holder 5. The switching valve is controlled by the system, and configured to control the airflow generated by a blower to flow, such that the patient will not be exposed to the air pressure if the switching valve is closed, and the patient will be prevented from any injury caused by airflow quickly flowing between related device and patient body when exposed to the air pressure if the switching valve is opened.

As shown in FIGS. 4 and 5, a chamber 1 includes a front cover 11 provided with a suction hole 15, a chamber body 12 and a rear cover 13 provided with a travel hole 17, in which the chamber 1, the chamber body 12 and the rear cover 13 are fasten-connected by bolts together; the chamber 1 is also provided with a driving air hole 14 at one side surface close to the front cover 11 and a free air hole 16 at an upper or side surface close to the rear cover 13; and the chamber 1 is further provided with a sealing washer 18 at both sides of the driving air hole 14. An air duct 2 is connected to the driving air hole 14. A direction-changing assembly 3 includes a spring 39, a mandril 32 and a direction-changing sliding block 31, in which the spring 39, located at a step inside the chamber 1, is pressed against the front cover 11 of the chamber 1 at one end and is in a contact with the direction-changing sliding block 31 at the other end; the mandril 32 is connected to the direction-changing sliding block 31 through the travel hole 17, and configured to move along an axis of the chamber 1 driven by the electric power driving device 4; the direction-changing sliding block 31, located inside the chamber 1, is in a sealing contact with an inner wall of the chamber 1 at its periphery, and configured to move in a linear reciprocation manner along the axis of the chamber 1 under alternative effects of the spring 39 and the mandril 32. The chamber 1 and the electric power driving device 4 are installed at the holder 5.

Preferably, the chamber 1 is in a detachable type.

In a second embodiment, as shown representatively in FIG. 3, the switching valve with the function of opening and closing pipeline according to the present disclosure may be controlled by the system, and configured to control the airflow with the air pressure generated by the blower to flow, such that the patient will not be exposed to the air pressure if the switching valve is closed, and the patient will be prevented from any injury caused by airflow quickly flowing between related device and patient body when exposed to the air pressure if the switching valve is opened.

As shown in FIGS. 4 and 5, a chamber 1 includes a front cover 11 provided with a suction hole 15, a chamber body 12 and a rear cover 13 provided with a travel hole 17, in which the chamber 1, the chamber body 12 and the rear cover 13 are fasten-connected by bolts together; the chamber 1 is also provided with a driving air hole 14 at one side surface close to the front cover 11 and a free air hole 16 at an upper or side surface close to the rear cover 13; and the chamber 1 is further provided with a sealing washer 18 at both sides of the driving air hole 14. An air duct 2 is connected to the driving air hole 14.

As shown in FIG. 6, the direction-changing assembly 3 includes the direction-changing sliding block 31, the mandril 32, a pushing block 33, a roller 34, a cam 35, a displacement sensor 36, a displacement turntable 37, a supporting platform 38 and the spring 39. The mandril 32 is connected to the direction-changing sliding block 31 through the travel hole 17 and configured to move along an axis of the chamber 1 driven by the electric power driving device 4. The direction-changing sliding block 31 located inside the chamber 1 is in a sealing contact with an inner wall of the chamber 1 at its periphery, and configured to move in a linear reciprocation manner along the axis of the chamber 1 under alternative effects of the spring 39 and the mandril 32.

As shown in FIG. 7, the cam 35 is fastened to the electric power driving device 4 at its bottom, so as to rotate under the power driving device 4, and fastened to the displacement turntable 37 at its top so as to rotate therewith.

As shown in FIG. 8, the pushing block 33 placed on the supporting platform 38 is provided with a first via hole 331, located at its upper surface close to a fourth end having an opening, through which the pushing block 33 is connected to a roller 34 rotate freely with a pivot 332; a second via hole 333, located at its right surface of a fifth end opposing to the fourth end, through which the pushing block 33 is connected to the mandril 32 in a plug-in manner; and a thread hole 334, located at its front surface close to the fifth end, through which the mandril 32 is fixed thereto by a bolt 335. The supporting platform 38, fixed on the holder 5, is configured to support the pushing block 33. The displacement sensor 36, fixed to the holder 5, is configured to detect the displacement turntable 37, for determining a rotating range of the electric power driving device 4. The spring 39, located at a step inside the chamber 1, is pressed against the front cover 11 of the chamber 1 at one end and is in a contact with the direction-changing sliding block 31 at the other end. The electric power driving device 4 is an electric motor. The chamber 1 and the electric power driving device 4 are installed at the holder 5.

Preferably, the chamber 1 is in a detachable type.

In a third embodiment, as shown in FIGS. 4 and 5, a chamber 1 includes a front cover 11 provided with a suction hole 15, a chamber body 12 and a rear cover 13 provided with a travel hole 17, in which the chamber 1, the chamber body 12 and the rear cover 13 are fasten-connected by bolts together; the chamber 1 is also provided with a driving air hole 14 at one side surface close to the front cover 11 and a free air hole 16 at an upper or side surface close to the rear cover 13; and the chamber 1 is further provided with a sealing washer 18 at both sides of the driving air hole 14. An air duct 2 is connected to the driving air hole 14. The direction-changing assembly 3 includes the direction-changing sliding block 31, the mandril 32, a cam 35, a displacement sensor 36, a displacement turntable 37, and the spring 39. The direction-changing sliding block 31, located inside the chamber 1, is in a sealing contact with an inner wall of the chamber 1 at its periphery, and configured to move in a linear reciprocation manner along the axis of the chamber 1 under alternative effects of the spring 39 and the mandril 32. The mandril 32 is connected to the direction-changing sliding block 31 through the travel hole 17, and is in a direct contact with the cam 35, such that the mandril 32 moves along the axis of the chamber 1 driven by the cam 35. The cam 35 is fastened to the electric power driving device 4 at its bottom so as to rotate under the electric power driving device 4; and fastened to the displacement turntable 37 at its top so as to rotate therewith. The displacement sensor 36, fixed to the holder 5, is configured to detect the displacement turntable 37, for determining a rotating range of the electric power driving device 4. The spring 39, located at a step inside the chamber 1, is pressed against the front cover 11 of the chamber 1 at one end and is in a contact with the direction-changing sliding block 31 at the other end. The electric power driving device 4 is an electric motor. The chamber 1 and the electric power driving device 4 are installed at the holder 5.

Preferably, the chamber 1 is in a detachable type.

In a fourth embodiment, as shown in FIG. 14, the direction-changing assembly 3 includes the direction-changing sliding block 31, the mandril 32 and the spring 39. The spring 39, located at a step inside the chamber 1, is pressed against the front cover 11 of the chamber 1 at one end and is in a contact with the direction-changing sliding block 31 at the other end. The mandril 32 is connected to the direction-changing sliding block 31 through the travel hole 17, and configured to move along an axis of the chamber 1 pushed by the electromagnet. The direction-changing sliding block 31, located inside the chamber 1, is in a sealing contact with an inner wall of the chamber 1 at its periphery, and configured to move in a linear reciprocation manner along the axis of the chamber 1 under alternative effects of the spring 39 and the mandril 32. The electric power driving device 4 is an electromagnet. The chamber 1 and the electric power driving device 4 are installed at the holder 5.

Preferably, the chamber 1 is in a detachable type.

Figure 10:
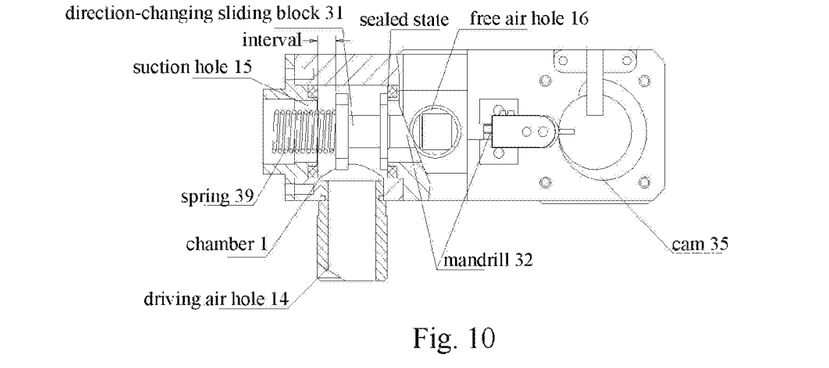
FIG. 10 is a schematic view showing an operation state of a switching valve configured to open and close pipeline according to an embodiment of the present disclosure.
Figure 11:
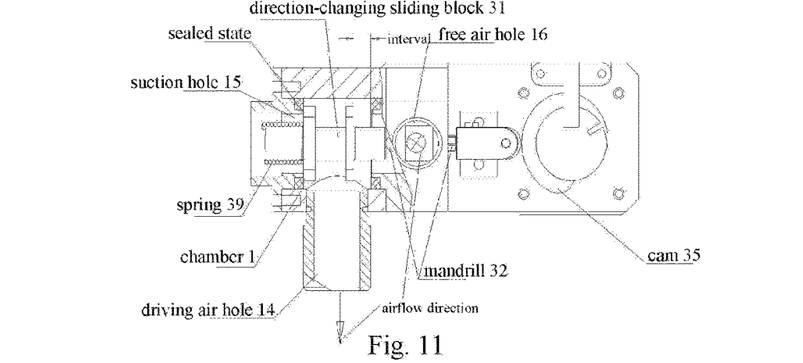
FIG. 11 is a schematic view showing an operation state of a switching valve configured to open and close pipeline according to an embodiment of the present disclosure.
Figure 12:
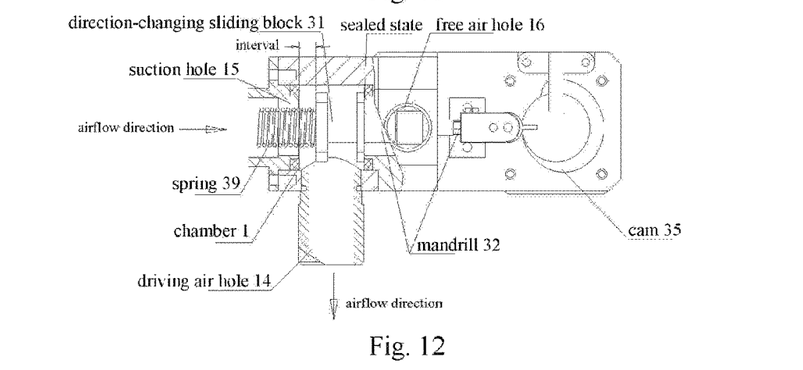
FIG. 12 is a schematic view showing an operation state of a switching valve configured to open and close pipeline according to an embodiment of the present disclosure.

In a fifth embodiment, a method for operating a switching valve configured to open and close pipeline according to the present disclosure includes the following steps. As shown in FIG. 10, in the case that the valve is in an initial state, the direction-changing sliding block 31 inside the chamber 1 is pressed against the sealing washer 18 close to the free air hole 16 under an elastic force of the spring 39 and in a stationary state. The spring 39 located between the suction hole 15 and the direction-changing sliding block 31 is in a slightly compressed state. As shown in FIG. 11, as soon as receiving a signal of pre-generating air pressure sent from the system, the electric motor 4 drives the cam 35 to rotate clockwise, the pushing block 33 drives the mandril 32 to move towards a front end of the chamber 1 under rotation effect of the cam 35 and the roller 34, such that the mandril 32 pushes the direction-changing sliding block 31 to move along an axis direction of the chamber forwards a front end thereof, and the direction-changing sliding block 31 is pressed against the sealing washer 18 close to the suction hole 15, so that the inside of the chamber 1 is separated from the outside of the suction hole 15, then at this time the spring 39 is in a compressed state. The direction-changing sliding block 31 is temporarily kept in a stationary state at such a position controlled by the displacement sensor 36. By this time, only the driving air hole 14 is communicated with the free air hole 16, and airflow flows into the driving air hole 14 from the free air hole 16, so as to form a pre-generated air pressure inside the chamber 1. As shown in FIG. 12, as soon as receiving a suction signal sent from the system, the electric motor 4 drives the cam 35 to move anticlockwise back to the initial state in cooperation of the displacement sensor 36, such that the direction-changing sliding block 31, the mandril 32 and the pushing block 33 are rebounded towards a rear end of the chamber under the elastic force of the spring 39 until a right end of the direction-changing sliding block 31 is pressed against the sealing washer 18 close to the free air hole 16, so as to separate the free air hole 16 from the chamber 1. By this time, the chamber 1 is communicated with the suction hole 15, and airflow gets into the driving air hole 14 from the suction hole 15 under effect of the pre-generated air pressure. The above processes may be repeated for customized times as required.

Figure 13:
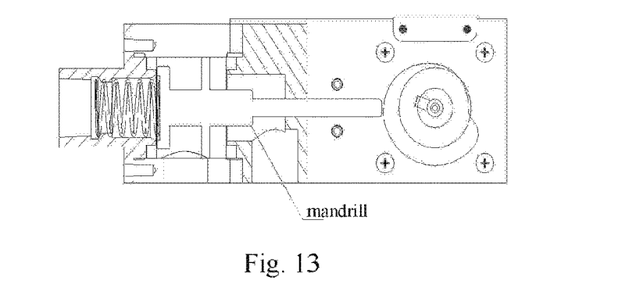
FIG. 13 is a schematic view showing an operation state of a switching valve configured to open and close pipeline according to an embodiment of the present disclosure.

In a sixth embodiment, another method for operating a switching valve configured to open and close pipeline according to the present disclosure includes the following steps. In the case that the valve is in an initial state, the direction-changing sliding block 31 inside the chamber 1 is pressed against the sealing washer 18 close to the free air hole 16 under an elastic force of the spring 39 and is in a stationary state. As shown in FIG. 13, as soon as receiving a signal of pre-generating air pressure sent from the system, the electric motor drives the cam 35 to rotate clockwise, such that the cam 35 pushes the mandril 32 (directly connected to the cam 35) to move towards a front end of the chamber 1 under a rotation effect of the cam 35, so as to further push the direction-changing sliding block 31 to move along the axis direction of the chamber 1 towards a front end thereof, for pressing against the sealing washer 18 close to the suction hole 15, so that the inside of the chamber 1 is separated from the outside of the suction hole 15, the at this time the spring 39 is in a compressed state. The direction-changing sliding block 31 is temporarily kept in a stationary state at such position controlled by the displacement sensor 36. By this time, only the driving air hole 14 is communicated with the free air hole 16, and airflow gets into the driving air hole 14 from the free air hole 16, so as to form a pre-generated air pressure in the chamber 1. As soon as receiving a suction signal sent from the system, the electric motor drives the cam 35 to move anticlockwise back to the initial state in cooperation of the displacement sensor 36, such that the direction-changing sliding block 31 and the mandril 32 are rebounded towards a rear end of the chamber under the elastic force of the spring 39 until a right end of the direction-changing sliding block 31 is pressed against the sealing washer 18 close to the free air hole 16, so as to separate the free air hole 16 from the chamber 1. By this time, the chamber 1 is communicated with the suction hole 15, and airflow gets into the driving air hole 14 from the suction hole 15 under effect of the pre-generated air pressure. The above processes may be repeated for customized times as required.

In a seventh embodiment, a further method for operating a switching valve configured to open and close pipeline according to the present disclosure includes the following steps. In the case that the valve is in an initial state, the direction-changing sliding block 31 inside the chamber 1 is pressed against the sealing washer 18 close to the free air hole 16 under an elastic force of the spring 39 and in a stationary state. The spring 39 located between the suction hole 15 and the direction-changing sliding block 31 is in a slight compressed state. As shown in FIG. 14, as soon as being charged, an electromagnet pushes the mandril 32 to move towards a front end of the chamber 1, so as to further push the direction-changing sliding block 31 to move along an axis direction of the chamber 1 to a front end thereof for pressing against the sealing washer 18 close to the suction hole 15, so that the direction-changing sliding block 31 is temporarily kept in a stationary state at such a position, then at this time the spring 39 is in a compressed state, the inside of the chamber 1 is separated from the outside of the suction hole 15, only the driving air hole 14 is communicated with the free air hole 16, and airflow gets into the driving air hole 14 from the free air hole 16, so as to form a pre-generated air pressure in the chamber 1. As soon as the electromagnet is cut off, the direction-changing sliding block 31 and the mandril 32 are rebounded towards a rear end of the chamber 1 under the elastic force of the spring 39 until a right end of the direction-changing sliding block 31 is pressed against the sealing washer 18 close to the free air hole 16, so as to separate the free air hole 16 from the chamber 1. By this time, the chamber 1 is communicated with the suction hole 15, and the airflow gets into the driving air hole 14 from the suction hole 15 under effect of the pre-generated air pressure. The above processes may be repeated for customized times as required.

In conclusion, the switching valve has the above-described technical features suitable for the field of respiratory gas exchange. The airway switching valve may cooperate with a breathing device to exchange airflow steadily and effectively to assist a patient in inhaling and exhaling and assist a patient to discharge secretions out of the airway, thus being suitable for a conjunction use with medical equipment such as a ventilator and being widely used in other related fields. Therefore, it could be expected that the application of the present disclosure may be promoted to use, thus obtaining benefits in multiple aspects such as economics and health at the same time.

The present disclosure provides an intelligent bionic system for expectorating sputum, configured to discharge secretions from patient's lung by mechanical ventilation. The airflow is inhaled at a positive pressure provide by a ventilator, and the respiratory muscle performs an inhaling movement under an effect of electrical or magnetic stimulation or mechanical stimulation. When intrapulmonary pressure reaches a certain threshold value, the airflow is converted to negative pressure inhaling, and at the time of exhaling the airflow quickly and shortly, the respiratory muscle performs a quick and short exhaling movement under the effect of electrical or magnetic stimulation or mechanical stimulation. During the entire processes of breathing, the movement of the respiratory muscle is synchronous with the inhaling and exhaling.

For a patient ventilated mechanically, at the time of simulating exhaling by introducing the negative pressure suction, the respiratory muscle synchronizing module is started at the same time, so as to facilitate the diaphragm muscle to contract or relax, thus increasing activity of the diaphragm muscle, improving strength of the diaphragm muscle, enhancing movements of cough and expectoration, increasing ventilation volume, enhancing oxygenation effect, improving function of ciliary movement in respiratory tract and facilitating secretions discharge.

Although explanatory embodiments have been described above, it would be appreciated by those skilled in the art that amendments and modifications can be made without departing from principles and spirit of the present disclosure, which are also regarded in the scope of the present disclosure.

What is claimed is:

1. An intelligent bionic system for expectorating sputum, comprising:
    a negative pressure suction module, configured to generate first airflow with a negative pressure;
    a three-way device, for connecting the negative pressure suction module to a patient and configured to allow the first airflow with the negative pressure generated from the negative pressure suction module and second airflow with a positive pressure to flow through;
    a central processing module, connected to the three-way device; and
    a respiratory muscle synchronizing module, connected to the central processing module and configured to enable a respiratory muscle to generate a certain movement in coordination with the first airflow and the second airflow, by means of nerve stimulation or mechanical stimulation;
    wherein the three-way device comprises a first valve that is a diaphragm valve configured to selectively block the second airflow through the three-way device, wherein the three-way device does not block the first airflow through the three-way device, and
    a second valve that is a shuttle valve is disposed between the three-way device and the negative pressure suction module and configured to selectively block the first airflow from the three-way device to the negative pressure suction module.

2. The intelligent bionic system for expectorating sputum according to claim 1, further comprising: a positive pressure ventilation module, connected to the three-way device and configured to generate the second airflow with the positive pressure.

3. The intelligent bionic system for expectorating sputum according to claim 2, wherein the three-way device is connected to a sputum collecting cup via a sputum collecting connector.

4. The intelligent bionic system for expectorating sputum according to claim 3, wherein when the positive pressure ventilation module is operating, the central processing module is configured to open the first valve and close the second valve, and to control the respiratory muscle synchronizing module to generate a muscle motion of inhaling.

5. The intelligent bionic system for expectorating sputum according to claim 3, wherein when the negative pressure suction module is operating, the central processing module is configured to open the second valve and close the first valve, and control the respiratory muscle synchronizing module to generate a muscle motion of cough.

6. The intelligent bionic system for expectorating sputum according to claim 5, wherein the first airflow with the negative pressure is of a flow rate allowed by the negative pressure suction module of 14 L/minute to 800 L/minute.

7. The intelligent bionic system for expectorating sputum according to claim 3, further comprising: a sensor module and a display module both connected to the central processing module.

8. The intelligent bionic system for expectorating sputum according to claim 7, wherein:
a first pressure detecting point of the sensor module is located at a side wall of a first branch of the three-way device directly connected to the positive pressure ventilation module,
a second pressure detecting point and a third pressure detecting point of the sensor module are located at a side wall of a second branch of the three-way device directly connected to the patient,
a distance between the second pressure detecting point and the patient is greater than that between the third pressure detecting point and the patient.

9. The intelligent bionic system for expectorating sputum according to claim 8, wherein the central processing module is configured to determine whether the first valve is closed based on pressure values detected at the first pressure detecting point and the third pressure detecting point.

10. The intelligent bionic system for expectorating sputum according to claim 9, wherein the central processing module determines that the first valve is closed when a pressure difference detected between the first pressure detecting point and the third pressure detecting point is beyond a threshold value.

11. The intelligent bionic system for expectorating sputum according to claim 8, wherein the central processing module is configured to calculate a flow rate and a direction of airflow breathed by the patient based on a pressure difference detected between the second pressure detecting point and the third pressure detecting point, and configured to determine whether the patient finishes inhaling or exhaling based on the flow rate and the direction of the airflow breathed by the patient obtained by calculating.

12. The intelligent bionic system for expectorating sputum according to claim 8, wherein upon starting cough, the central processing module is configured to control the negative pressure suction module and respiratory muscle synchronizing module to work in a synchronizing and cooperating manner such that:
during an inhaling stage, at a time that the first valve is opened and the second valve is closed, the respiratory muscle synchronizing module generates a contraction action of the diaphragm muscle, such that the patient inhales more sufficiently, getting ready for valid cough;
when it is determined that the patient finishes inhaling as detected by the sensor module at the pressure detecting points, the second valve is opened and the first valve is closed, the respiratory muscle synchronizing module generates a contraction action of the abdominal muscle, thus simulating cough in terms of airflow and muscle movement, so that a better effect of discharging secretions from lung is achieved; and
when it is determined that patient finishes exhaling as detected by the sensor module at the pressure detecting points, the second valve is closed and the first valve is opened, so as to start a new breathing cycle.

13. The intelligent bionic system for expectorating sputum according to claim 3, wherein the first valve is a pneumatic diaphragm valve.

14. The intelligent bionic system for expectorating sputum according to claim 3, wherein the second valve is configured to control the first airflow with a negative pressure to flow-through or cut-off, wherein the second valve is an electric-controlled switching valve, and the second valve comprises:
a holder,
an electric power driving device, installed at the holder,
a cavity, also installed at the holder and comprising a front cover provided with a suction hole; a cavity body; and a rear cover provided with a travel hole, wherein:
the front cover, the cavity body and the rear cover are fasten-connected by bolts together;
the cavity is also provided with a driving hole at one side surface close to the front cover and a free air hole at an upper or side surface close to the rear cover;
and the cavity is further provided with sealing washers at opposite sides of the driving hole,
an air duct, connected to the driving hole,
a direction-changing assembly, comprising a spring, a mandril and a direction-changing sliding block, wherein
the spring, located at a step inside the cavity, is pressed against the front cover of the cavity at one end and is in a contact with the direction-changing sliding block at the other end;
the mandril is connected to the direction-changing sliding block through the travel hole, and configured to move along an axis of the cavity under a drive of the electric power driving device;
the direction-changing sliding block, located inside the cavity, is in a sealing contact with an inner wall of the cavity at a periphery of the direction-changing sliding block, and configured to move in a linear reciprocation manner along the axis of the cavity under alternative effects of the spring and the mandril.

15. The intelligent bionic system for expectorating sputum according to claim 14, wherein the cavity is a detachable type.

16. The intelligent bionic system for expectorating sputum according to claim 14, wherein:
the direction-changing assembly comprises the direction-changing sliding block, the mandril, a pushing block, a roller, a cam, a displacement sensor, a displacement turntable, a supporting platform and the spring,
the electric power driving device is an electric motor,
the pushing block, placed on the supporting platform, is provided with:
a first via hole, located at an upper surface of the pushing block close to a fourth end having an opening, through which the pushing block is connected to the roller rotated freely with a pivot;
a second via hole, located at an end surface of the pushing block at a fifth end opposing to the fourth end, through which the pushing block is connected to the mandril in a plug-in manner; and
a thread hole, located at a side surface of the pushing block close to the fifth end, through which the mandril is fixed thereto by a bolt,
the supporting platform, fixed on the holder, is configured to support the pushing block,
the cam is fastened to the electric power driving device at a bottom of the cam, so as to rotate under a drive of the electric power driving device; and fastened to the displacement turntable at a top of the cam so as to rotate therewith, and the displacement sensor, fixed on the holder, is configured to detect the displacement turntable, for determining a rotating range of the electric power driving device.

17. The intelligent bionic system for expectorating sputum according to claim 14, wherein:
the direction-changing assembly comprises the direction-changing sliding block, the mandril, a cam, a displacement sensor, a displacement turntable and the spring, the electric power driving device is an electric motor;
the cam is fastened to the electric power driving device at a bottom of the cam so as to rotate under a drive of the electric power driving device; and fastened to the displacement turntable at a top of the cam so as to rotate therewith,
the mandril is in a direct contact with the cam, such that the mandril moves along the axis of the cavity under a drive of the cam;
the displacement sensor, fixed on the holder, is configured to detect the displacement turntable, for determining a rotating range of the electric power driving device.

18. The intelligent bionic system for expectorating sputum according to claim 14, wherein: the direction-changing assembly comprises the direction-changing sliding block, the mandril and the spring; the electric power driving device is an electromagnet; and the mandril is configured to move along the axis of the cavity under a push of the electromagnet.

19. The intelligent bionic system for expectorating sputum according to claim 2, wherein the positive pressure ventilation module is a ventilator.

20. The intelligent bionic system for expectorating sputum according to claim 2, wherein the three-way device comprises a first part, a second part, a pressing cover, the diaphragm valve, an air-resistor, wherein:
the first part comprises a second end for connecting the positive pressure ventilation module, a first end for connecting the negative pressure suction module, a first pressure detecting point and a groove;
the second part comprises a third end for connecting the patient, an internal thread, a second pressure detecting point and a third pressure detecting point, and a snap; and
the pressing cover comprises an external thread and an air supply hole.

21. The intelligent bionic system for expectorating sputum according to claim 1, wherein the nerve stimulation is by way of electrical stimulation or magnetic stimulation,
wherein the electrical stimulation is executed by a pair of treating electrodes acting on both sides of phrenic nerves and a pair of reference electrodes acting on a surface of pectoralis major muscle; and
the magnetic stimulation is executed by discharging from a capacitor stored with electric energy to stimulate coils such that a pulse current is generated.

22. The intelligent bionic system for expectorating sputum according to claim 1, wherein the mechanical stimulation is executed by different pushes acting on the respiratory muscle with a mechanical arm, in corporation with inhaling and exhaling,
wherein the different pushes are generated in the light of a control signal from the central processing module.

* * * * *